(12) United States Patent
Matsushita et al.

(10) Patent No.: US 8,993,254 B2
(45) Date of Patent: Mar. 31, 2015

(54) METHODS FOR EVALUATING RISK OF MOTHER'S MILK OR FOOD INDUCING AN ONSET OF ATOPIC DERMATITIS, AND MOTHER'S MILK OR FOOD WITH REDUCED RISK OF INDUCING AN ONSET OF ATOPIC DERMATITIS

(75) Inventors: Sho Matsushita, Iruma-gun (JP); Takehiro Higashi, Iruma-gun (JP)

(73) Assignee: Saitama Medical University, Saitama (JP)

( * ) Notice: Subject to any disclaimer, the term of this patent is extended or adjusted under 35 U.S.C. 154(b) by 0 days.

(21) Appl. No.: 13/504,413

(22) PCT Filed: Oct. 26, 2010

(86) PCT No.: PCT/JP2010/068974
§ 371 (c)(1),
(2), (4) Date: Apr. 26, 2012

(87) PCT Pub. No.: WO2011/052592
PCT Pub. Date: May 5, 2011

(65) Prior Publication Data
US 2012/0214183 A1    Aug. 23, 2012

(30) Foreign Application Priority Data
Oct. 29, 2009 (JP) .................... 2009-248505

(51) Int. Cl.
*G01N 33/00* (2006.01)
*G01N 33/68* (2006.01)

(52) U.S. Cl.
CPC ........ *G01N 33/6893* (2013.01); *G01N 2333/90* (2013.01); *G01N 2800/02* (2013.01); *G01N 2800/202* (2013.01); *Y10S 436/824* (2013.01)
USPC ............ 435/7.92; 436/20; 436/501; 436/824

(58) Field of Classification Search
CPC combination set(s) only.
See application file for complete search history.

(56) References Cited

U.S. PATENT DOCUMENTS

| | | | |
|---|---|---|---|
| 3,935,072 A | | 1/1976 | Chibata et al. |
| 4,208,479 A | * | 6/1980 | Zuk et al. ............. 435/7.9 |
| 2002/0142347 A1 | * | 10/2002 | Knudsen et al. ........... 435/7.1 |

FOREIGN PATENT DOCUMENTS

| | | | | |
|---|---|---|---|---|
| GB | 1440369 | * | 8/1972 | ............ C07H 19/20 |
| JP | 49-035584 A | | 4/1974 | |
| JP | 3780283 B2 | | 5/2006 | |
| WO | 2006/054415 A1 | | 5/2007 | |

OTHER PUBLICATIONS

Nutricia Neocate (retrieved from URL:www.neocate.com/about-neocate/neocate-formula on Jul. 18, 2013).*
Greer et al., (Pediatrics vol. 121 No. 1 Jan. 1, 2008).*
Daugherty et al., J. Biol. Chem. 2002, 277:21431-21439.*
Bartlett et al., J. Biol. Chem. 1956, 218:419-424.*
Cooperstein et al., 1957; J Biol Chem. Jun. 1958;232(2):695-703.*
Van Aardt et al.,Agric. Food Chem. 2001;vol. 49, pp. 1377-1381.*
Hibbitt et al., Journal of Dairy Research , vol. 31, Issue 01 ,Feb. 1964, pp. 105-112.*
International Preliminary Report on Patentability dated Jun. 21, 2012 in corresponding PCT Patent Application No. PCT/JP2010/068974.
Higashi, Takehiro, et al., "Adjunvant Kassei no Tayosei to sono Oyo," Journal of Saitama Medical Univerisity, Sep. 2009, pp. 33-35, vol. 36, No. 1.
Higashi, Takehrio, et al., "Atopic Dermatitis Kanji Sesshu Bonyu no Shikenkan-nai Adjuvant Kassei Hyokacho, Mochiita Cohort Kenkyu," Japanese Journal of Allergology, Oct. 30, 2008, pp. 1407, vol. 57, No. 9/10.
Higashi, Takehiro, et al., "Atopic Dematitis Kanji ga Sesshu shita Bonyu ni Fukumareru Th2 Adjuvant Kassei Busshitsu no Dotei," Japanese Journal of Allergology, Oct. 25, 2010, pp. 1269, vol. 59, No. 9/10.
Takeda, Kiyoshi, et al., "Toll receptors and pathogen resistance," Cellular Microbiology, 2003, pp. 143-153, vol. 5, No. 3.
Van Der Kleij, et al., "A Novel Host-Parasite Lipid Cross-take: Schistosomal Lyso-Phosphatidyserine Acitivities Toll-Like Receptor 2 and Affects Immune Polarization," The Journal of Biological Chemistry, Dec. 13, 2002, pp. 48122-48129, vol. 277, No. 50.
International Search Report for PCT/JP2010/068974 dated Dec. 28, 2010.

* cited by examiner

Primary Examiner — Shafiqul Haq
Assistant Examiner — Carmencita M Belei
(74) Attorney, Agent, or Firm — Sughrue Mion, PLLC

(57) ABSTRACT

An entity of a Th2 adjuvant activity in mother's milk has been revealed as coenzyme A by HPLC and mass spectrometry. The followings have been found out that: a risk of developing atopic dermatitis can be evaluated by targeting coenzyme A; and any one of a food and mother's milk with a reduced risk of developing atopic dermatitis can be prepared by removing or inactivating coenzyme A.

2 Claims, 4 Drawing Sheets

METHODS FOR EVALUATING RISK OF MOTHER'S MILK OR FOOD INDUCING AN ONSET OF ATOPIC DERMATITIS, AND MOTHER'S MILK OR FOOD WITH REDUCED RISK OF INDUCING AN ONSET OF ATOPIC DERMATITIS

CROSS REFERENCE TO RELATED APPLICATION

This application is a National Stage of International Application No. PCT/JP2010/068974, filed Oct. 26, 2010, which claims priority from JP 2009-248505, filed on Oct. 29, 2009, the contents of all of which are incorporated herein by reference in their entirety.

TECHNICAL FIELD

The present invention relates to a method for evaluating a risk of any one of mother's milk and a food inducing an onset of atopic dermatitis, and to any one of mother's milk and a food with a reduced risk of inducing an onset of atopic dermatitis. More specifically, the present invention relates to a method for evaluating a risk of any one of mother's milk and a food inducing an onset of atopic dermatitis, the method targeting coenzyme A, and to any one of a food and mother's milk with a reduced risk of inducing an onset of atopic dermatitis by removing or inactivating coenzyme A.

BACKGROUND ART

Recently, it has become more and more apparent that dendritic cells (DC) play an important role as an interface between an environmental factor and an immune response. Dendritic cells are cells differentiated from monocytes of hematopoietic stem cell origin, and known as major antigen-presenting cells (APCs) together with macrophages and B cells. Only dendritic cells do function as professional APCs capable of inducing a primary response of naive T cells by presenting an antigen to the naive T cells. Particularly, antigen presentation by dendritic cells is essential to induce differentiation into helper T cells (Th cells). In the antigen presentation by dendritic cells, a protein antigen incorporated by phagocytosis is fragmented into peptides, and the peptides (antigenic peptides) are bound to MHC class I molecules or MHC class II molecules and thus transported to the surfaces of the dendritic cells.

Meanwhile, there is known an active substance other than a protein antigen involved in antigen presentation as described above. Unlike a protein antigen, the active substance increases the antigen-presenting function of dendritic cells irrespectively of the type of antigen and enhances an immune response. Such a substance is called an adjuvant. A portion of an adjuvant binds to a specific, TOLL-like receptor (TLR) on the surface of an immature dendritic cell (immature DC: iDC). The signal is transmitted into the cell, and thereby the immature dendritic cell is activated and differentiated into a mature dendritic cell (mature DC: mDC) (see, for example, NPL 1). Several types of mature dendritic cell are known, which respectively have different differentiation-inducing activities on naive CD4-positive T cells. Generally, a mature dendritic cell inducing a Th1 (T helper 1) cell is called DC1; a mature dendritic cell inducing a Th2 (T helper 2) cell is called DC2; a mature dendritic cell inducing a Th17 (T helper 17) cell is called DC17; and a mature dendritic cell inducing a Tr (T regulatory) cell is called DCr. Moreover, an adjuvant having an activity of differentiating an immature dendritic cell into DC1 is called a Th1 adjuvant; an adjuvant having an activity of differentiating an immature dendritic cell into DC2 is called a Th2 adjuvant; an adjuvant having an activity of differentiating an immature dendritic cell into DC17 is called a Th17 adjuvant; and an adjuvant having an activity of differentiating an immature dendritic cell into DCr is called a Tr adjuvant.

A lipopolysaccharide (LPS) principally produced by a bacterium, and the like are known as the Th1 adjuvant; phosphatidylserine that is a phospholipid derived from a schistosome, and the like are known as the Th2 adjuvant; curdlan and the like are known as the Th17 adjuvant; and lysophosphatidylserine and the like are known as the Tr adjuvant (see, for example, NPL 2).

It is known that many immune diseases occur when the equilibrium state of the function of Th cells is disturbed (Th imbalance). For example, autoimmune diseases such as type 1 diabetes are known as diseases caused by excessive activation of Th1 cells, and allergic diseases such as atopic dermatitis and asthma are known as diseases caused by excessive activation of Th2 cells. Thus, into which Th cell an adjuvant has an activity of inducing the differentiation of a naive CD4-positive T cell is important in immune response reactions and also in treatment of immune diseases.

Among specified substances such as environmental substances and chemical substances surrounding our lives, there are many substances having an activity of modifying an immune response as an adjuvant. Indeed, some of these specified substances are known as causative factors of allergic diseases such as atopicdermatitis, pollen allergy, and bronchial asthma, threatening human healthy lives at present. Thus, evaluating the adjuvant activity of a specified substance, particularly evaluating on which Th cell a specified substance has the adjuvant activity, is important in predicting the influence of specified substances on a human body. Moreover, it is also quite important in checking the safety of manufactured products and the like including specified substances, and checking the efficacy of drugs and the like including specified substances.

For this reason, the present inventors have developed a method for evaluating an adjuvant activity on Th cells using dendritic cells (Patent Literature 1). Further, an association has been found out between atopic dermatitis and a Th2 adjuvant activity in mother's milk as a result of detecting the Th2 adjuvant activity in mother's milk taken by infants who developed atopic dermatitis using THP-1 cells as dendritic cells (NPL 3).

However, an entity of the Th2 adjuvant activity in mother's milk has not been revealed yet.

CITATION LIST

Patent Literature

[PTL 1] International Publication No. WO2006/054415

Non Patent Literatures

[NPL 1] Takeda K, Akira S. Cell Microbiol 5: 143-153, 2003
[NPL 2] van der Kleij D, et al., J Biol Chem. 277(50): 48122-48129, 2002
[NPL 3] Japanese Journal of Allergology, Vol. 57, Nos. 9 and 10, the 58th fall meeting of Japanese Society of Allergology, "Cohort Study of Mother's Milk Taken by Infant Patients with Atopic Dermatitis Using Method for Evaluating Adjuvant Activity In Vitro," Japanese Society of Allergology, p. 1407, Oct. 30, 2008.

SUMMARY OF INVENTION

Technical Problems

The present invention has been made in view of such circumstance. An object of the present invention is to identify an entity of a Th2 adjuvant activity in mother's milk. Another object of the present invention is to provide a method for evaluating a risk of developing atopic dermatitis by targeting the identified entity of the Th2 adjuvant activity, and to provide any of a food and mother's milk with a reduced risk of developing atopic dermatitis by removing or inactivating the entity.

Solution to Problems

In order to achieve the above objects, the present inventors first attempted to purify, by high-performance liquid chromatography (HPLC), an entity of a Th2 adjuvant activity in mother's milk of infant patients who developed atopic dermatitis at 6 months after birth. As a result, it was revealed that the activity was recovered in the liquid phase of mother's milk and eluted as a single fraction by reversed phase-HPLC. The present inventors next conducted mass spectrometry on this fraction. In the mass spectrometry, many signals were detected. Among them, it was revealed that a signal of "Mi=384.7719, Mi+1=385.2754 (Mi+1−Mi=0.5035)" was detected in mother's milk having a high Th2 adjuvant activity but not detected in mother's milk having a low Th2 adjuvant activity. The molecular weight of this signal molecule was determined to be 767.5292. The molecular weight completely matched the molecular weight of coenzyme A. To support that coenzyme A was an entity of a Th2 adjuvant activity in mother's milk, the present inventors next measured the Th2 adjuvant activity of coenzyme A in a system developed by themselves. As a result, it was revealed that coenzyme A even at a low concentration exhibited a Th2 adjuvant activity in vitro. Moreover, it was demonstrated that the concentration of coenzyme A in mother's milk had a clear correlation with atopic dermatitis of infant patients. Further, the Th2 adjuvant activity of coenzyme A was also found in an experiment using mice to which coenzyme A was orally administered. The above suggested that coenzyme A contained in mother's milk taken immediately after birth induced an onset of atopic dermatitis of infants.

Since the relation between coenzyme A and induction of an onset of atopic dermatitis was demonstrated, the present inventors have found out that it is possible to evaluate a risk of any one of mother's milk and a food inducing an onset of atopic dermatitis by targeting coenzyme A; and it is possible to prepare any one of mother's milk and a food with a reduced risk of inducing an onset of atopic dermatitis by removing or inactivating coenzyme A.

The present invention is based on the finding, and more specifically provides the following inventions.
(1) A method for evaluating a risk of any one of mother's milk and a food inducing an onset of atopic dermatitis, the method characterized by comprising
detecting coenzyme A in any one of mother's milk and a food.
(2) A method for preparing any one of mother's milk and a food with a reduced risk of inducing an onset of atopic dermatitis, the method characterized by comprising
removing or inactivating coenzyme A in any one of mother's milk and a food.
(3) Any one of mother's milk and a food prepared by the method according to (2), wherein
coenzyme A is removed or inactivated.
(4) A kit used for the method according to (1), the kit comprising any one of (a) and (b) below:
(a) a substance which binds to coenzyme A; and
(b) a solid phase to which the substance of (a) binds.
(5) An instrument used for the method according to (1), the instrument comprising any one of (a) and (b) below binding thereto;
(a) a substance which binds to coenzyme A; and
(b) a solid phase to which the substance of (a) binds.
(6) An apparatus used for the method according to (1), the apparatus comprising the instrument according to (5).
(7) A kit used for the method according to (2), the kit comprising any one of (a) and (b) below:
(a) any one of a substance which binds to coenzyme A and a substance which inactivates coenzyme A; and
(b) a solid phase to which the substance of (a) binds.
(8) An instrument used for the method according to (2), the instrument comprising any one of (a) and (b) below binding thereto:
(a) any one of a substance which binds to coenzyme A and a substance which inactivates coenzyme A; and
(b) a solid phase to which the substance of (a) binds.
(9) An apparatus used for the method according to (2), the apparatus comprising the instrument according to (8).

Advantageous Effects of Invention

The present invention has revealed a relation between coenzyme A and induction of an onset of atopic dermatitis. This makes it possible to efficiently evaluate a risk of any one of mother's milk and a food inducing an onset of atopic dermatitis by targeting coenzyme A. Moreover, it is made possible to efficiently prepare anyone of mother's milk and a food with a reduced risk of inducing an onset of atopic dermatitis by removing or inactivating coenzyme A.

DESCRIPTION OF EMBODIMENTS

Figure 1:
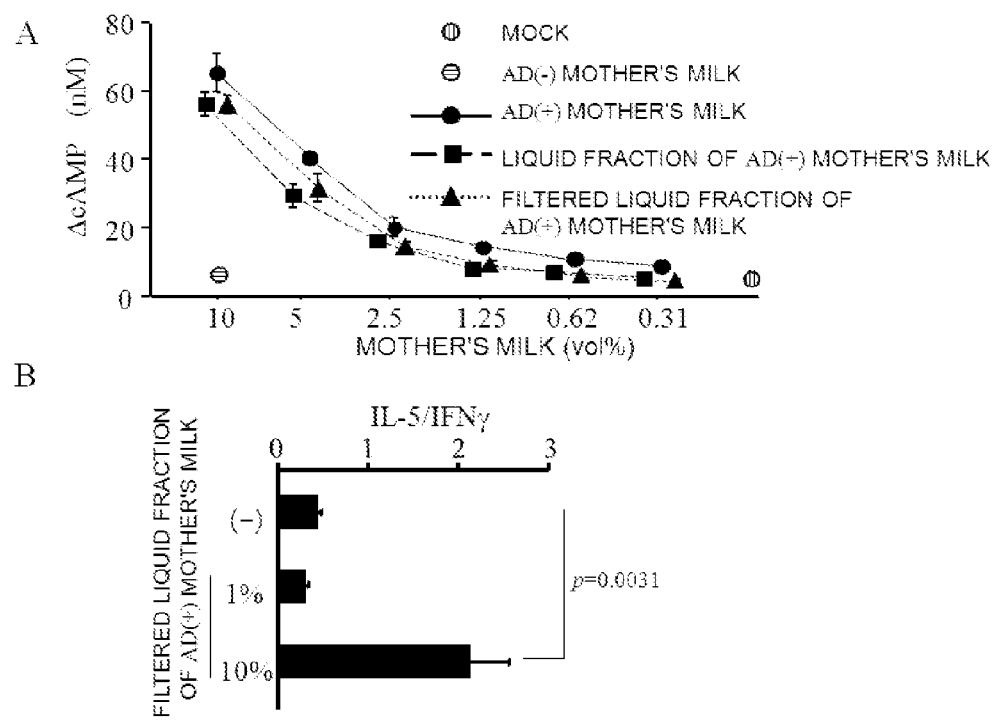
FIG. 1 is graphs showing the result of detecting a Th2 adjuvant activity in fractionated mother's milk. Part A shows the result of detecting the Th2 adjuvant activities, on the basis of cAMP, of fractions of the mother's milk sample separated by centrifugation into: a surface lipid, an interface liquid phase, and a pellet. Part B shows the result of detecting the Th2 adjuvant activity, on the basis of IL-5/IFN$_\gamma$, of a liquid fraction filtered from mother's milk of a group (AD(+)) who developed atopic dermatitis at 6 months after birth.

The present invention is based on the finding of the present inventors that: coenzyme A has a Th2 adjuvant activity, and the intake thereof may induce an onset of atopic dermatitis. Thus, the present invention provides a method for evaluating a risk of any one of mother's milk and a food inducing an onset of atopic dermatitis, the method characterized by comprising detecting coenzyme A in any one of mother's milk and a food.

The "mother's milk" used in the method of the present invention is not particularly limited, and it is possible to use any mother's milk whose risk of inducing an onset of atopic dermatitis is desired to be evaluated. As the mother's milk, it is possible to target those derived from various mammals such as human, monkey, cattle, sheep, horse, dog, mouse, and rat. When a risk of inducing an onset of atopic dermatitis is evaluated for human infants, the mother's milk is preferably one obtained immediately after delivery. Herein, the phrase "immediately after delivery" means 2 weeks or less after delivery, preferably 1 week or less (for example, 4 days or less). The method of the present invention makes it possible to evaluate a risk of developing atopic dermatitis of infants who take mother's milk obtained immediately after delivery by detecting coenzyme A in the mother's milk.

The "food" used in the method of the present invention is not particularly limited, and it is possible to use any food whose risk of inducing an onset of atopic dermatitis is desired to be evaluated. Examples of the food include foods, health foods, functional foods, nutritional supplementary foods, foods for specified health use, quasi drugs, and the like. Specifically, the followings can be included: artificial milk and baby foods for infants, dairy products such as yogurts and milk drinks, juices, confections, noodles, cereals, convenience foods, supplements, and the like.

Coenzyme A detected in any one of mother's milk and a food can be measured by known methods such as, for example, enzyme immunoassay and western blotting using an antibody specific to coenzyme A. The antibody against coenzyme A may be a polyclonal antibody or a monoclonal antibody, as long as the antigen is capable of recognizing it. The antibody against coenzyme A can be produced according to known methods for producing an antibody or an antiserum using coenzyme A as an antigen. For example, the polyclonal antibody can be produced by: immunizing animal to be immunized such as rabbit with coenzyme A; collecting a blood therefrom after a certain period; and removing a blood clot. Meanwhile, the monoclonal antibody can be produced by: fusing a bone tumor cell to an antibody-producing cell of an animal immunized with coenzyme A; and isolating monoclone cells (hybridoma) producing the target antibody to obtain the antibody from the cells. In the immunization, coenzyme A can be used while binding to a carrier protein having an antigenic stimulus, such as KLH, if necessary.

Coenzyme A detected in any one of mother's milk and a food can be detected using a substance which binds to coenzyme A, other than the above-described antibodies. Examples of such a substance include proteins (including enzymes) which bind to coenzyme A. Examples of the enzymes which bind to coenzyme A include dephospho-CoA kinase, acetyl-transferase, acyl-CoA reductase, palmitoyl-CoA hydrolase, acetyl-CoA hydrolase, citrate synthase, and mixtures thereof.

In detecting coenzyme A, the antibodies and other substances which bind to coenzyme A, if necessary, may be labeled as appropriate. The label is not particularly limited, as long as detectable. Examples thereof include fluorescent labels, enzyme labels, and radiolabels.

Coenzyme A detected in any one of mother's milk and a food can be detected based on the coenzyme activity of coenzyme A. Examples of the coenzyme activity serving as the detection target include acyl group (for example, acetyl group)-transferring activities (see E. R. STADTMAN, et al., J. Biol. Chem. 191(1): 365-76, 1951). The use of a commercially-available kit enables convenient detection of such coenzyme activities. For example, when Coenzyme A Assay kit (BioVision Research Products) is used, a substance produced by the coenzyme activity of coenzyme A reacts with an OxiRed probe to generate color ($\lambda$=570 nm) and fluorescence (Ex=535/Em=587 nm); accordingly, by measuring these, the concentration of coenzyme A can be quantified.

Furthermore, as described in the present examples and Japanese Patent No. 3780283, coenzyme A can be detected by LC-MS techniques. For example, reversed-phase chromatography is carried out using a silica gel base to which an octyl-silane group (C8) is bonded. Then, a predetermined fraction which is eluted by a TFA-acetonitrile concentration gradient, and which is considered to contain coenzyme A, is analyzed with a mass spectrometer. In this manner, the peak of coenzyme A can be detected.

In the method of the present invention, as a result of evaluating mother's milk or a food by the above-described method, if the mother's milk or the food is evaluated as containing a significant concentration or amount of coenzyme A, the mother's milk or the food is evaluated as having a risk of inducing an onset of atopic dermatitis.

Herein, the term "significant concentration or amount" means a concentration or amount at a risk level of inducing an onset of atopic dermatitis. For example, when mother's milk is used in the method of the present invention, a value of coenzyme A concentration in mother's milk for an infant who does not develop atopic dermatitis is used as a control. If the coenzyme A concentration in mother's milk is higher than this control value (preferably, 2-fold or higher, more preferably 3-fold or higher, and further preferably 5-fold or higher), the mother's milk sample is evaluated as having a risk of inducing an onset of atopic dermatitis. Generally, if coenzyme A is contained at a concentration of 0.5 nM or higher in mother's milk obtained immediately after delivery, it is evaluated as having a risk of inducing an onset of atopic dermatitis. If the concentration is 1.0 nM or higher, the risk of inducing an onset of atopic dermatitis is evaluated as being high. Based on this evaluation, it is possible to prevent an onset of atopic dermatitis of infants.

The present invention also provides a method for preparing any one of mother's milk and a food with a reduced risk of inducing an onset of atopic dermatitis, the method characterized by comprising removing or inactivating coenzyme A in any one of mother's milk and a food.

In the method of the present invention, to remove coenzyme A from any one of mother's milk and a food, for example, a substance which binds to coenzyme A can be used. Examples of such a substance include the above-described antibodies against coenzyme A and the above-described enzymes which bind to coenzyme A. These antibodies and enzymes or extracts from microorganisms producing coenzyme A are bound to, for example, water-insoluble polysaccharides activated with a cyanogen halogen (for example, spharose, sephadex, dextran, agarose, and the like activated with cyanogen bromide, cyanogen iodide, or cyanogen chloride), and can be used in affinity purification for coenzyme A (Japanese Patent Application Publication No. Sho 49-35584, U.S. Pat. No. 3,935,072). Moreover, to inactivate coenzyme A in any one of mother's milk and a food, for example, a substance which inactivates coenzyme A can be used. An example of such a substance is alloxan (S. J. COOPERSTEIN., J. Biol. Chem. 232: 695-704, 1958). Alloxan directly reacts with coenzyme A and inhibits an acetylation reaction. Besides, ethanol, acetaldehyde, and nitrogen monoxide are known to inactivate coenzyme A (H. P. T. Ammon, et al., Biochem. Pharmacol. 18(1): 29-33, 1969, W. E. W. Roediger, Digestion 65: 191-195, 2002). These can also be used in the present invention.

Note that, in the present invention, the "substance which inactivates coenzyme A," when having an activity of binding to coenzyme A, also serves as a "substance which binds to coenzyme A." Moreover, the "substance which binds to coenzyme A," when having an activity of inactivating coenzyme A, also serves as a "substance which inactivates coenzyme A."

As long as the substance which binds to coenzyme A or the substance which inactivates coenzyme A is capable of binding to a solid phase, when mother's milk and a food (including materials, intermediates in the preparation process, and the like) are applied to the solid phase with such a substance binding thereto, such a substance is capable of removing coenzyme A from mother's milk and a food or inactivating coenzyme A contained in mother's milk and a food. When mother's milk and a food are applied to the solid phase, preferably these are dissolved in distilled water, a buffer solution, a water-soluble solvent, or the like in advance, and an impurity and a precipitate are removed by centrifugation or the like.

The solid phase used in the present invention is a solid having a surface to which the substance for removing or inactivating coenzyme A can bind. The surface is preferably a hydrophobic surface. Examples of the solid phase include silica particles, filters, solid phase extraction column, polymer materials, filter materials, polystyrene beads, magnetic fine particles, latexes, or these having a processed surface.

In the present invention, various methods can be selected to remove or inactivate coenzyme A. For example, in a case of using a particulate solid phase with the substance for removing or inactivating coenzyme A binding thereto, coenzyme A can be removed by a batch method. Specifically, the solid phase is suspended in a sample solution. Then, a complex of coenzyme A with the solid phase is precipitated, and a liquid component is separated therefrom. In this manner, coenzyme A can be removed. In this precipitation process, besides the gravitational precipitation, the precipitation can also be achieved by a centrifugation operation. Alternatively, the particulates may be provided with a property of being pulled to a magnet to carryout the precipitation operation through the attraction to a magnet.

Moreover, in a case of using a filter-form solid phase or a column-form solid phase, coenzyme A can be removed or inactivated by a filter transmission method. In this case, while a sample is transmitted through the filter or the column, the sample comes into contact with the solid phase to which the substance for removing or inactivating coenzyme A binds.

Further, by using the following instrument to which any one of mother's milk and food samples is applied, it is also possible to remove or inactivate coenzyme A contained in the samples, the instrument comprising any one of the followings binding thereto:

the substance for removing or inactivating coenzyme A; and the solid phase to which the substance binds (the instrument is for example a container such as a flask, a beaker, or a tank having a surface processed with the substance or the solid phase, a column packed with the substance or the solid phase, or the like).

Furthermore, the method of the present invention can be conveniently carried out by using the following apparatus comprising the instrument installed therein. Specifically, a sample is injected into a sample-injection port of the apparatus, and the injected sample comes into contact with the substance, on the instrument, for removing or inactivating coenzyme A; thus, the sample in which coenzyme A is removed or inactivated is collected from a discharge port of the apparatus. For example, in a case of using a column packed with the solid phase to which substance for removing or inactivating coenzyme A binds, the apparatus may comprise: a device such as a pump or gas cylinder for forming the flow of a sample solution in the column; a device for adjusting temperature or treatment time; and the like.

When the substance for inactivating coenzyme A is used, coenzyme A contained in any one of mother's milk and a food can be inactivated by adding the substance to the any one of mother's milk and a food. In this case, the substance for inactivating coenzyme A is desirably not harmful in the body of a mammal that takes it.

The present invention provides any one of mother's milk and a food prepared by the above-described the method of the present invention, wherein coenzyme A is removed or inactivated. Such any one of mother's milk and a food is useful as mother's milk or a food with a reduced risk of inducing an onset of atopic dermatitis. The any one of mother's milk and a food of the present invention is believed to be high in efficacy particularly when taken by infants.

Moreover, the present invention provides a kit used for the method for evaluating a risk of any one of mother's milk and a food inducing an onset of atopic dermatitis of the present invention, or the method for preparing any one of mother's milk and a food with a reduced risk of inducing an onset of atopic dermatitis of the present invention.

The kit of the present invention comprises any one of:

the above-described substance which binds to coenzyme A; and a solid phase to which the substance binds. If necessary, by appropriate labeling as described above, these serve as a reagent (or an effective component thereof) for evaluating the risk of any one of mother's milk and a food inducing an onset of atopic dermatitis. When used for the method for preparing any one of mother's milk and a food with a reduced risk of inducing an onset of atopic dermatitis, the kit may use the above-described substance which inactivates coenzyme A in place of the substance which binds to coenzyme A. The kit of the present invention may further comprise an instruction therefor.

Further, the present invention provides an instrument used for the method for evaluating a risk of any one of mother's milk and a food inducing an onset of atopic dermatitis of the present invention, or the method for preparing any one of mother's milk and a food with a reduced risk of inducing an onset of atopic dermatitis of the present invention.

The instrument of the present invention comprises any one of the followings binding thereto:

a substance which binds to the above-described coenzyme A; and a solid phase to which the substance binds. When used for the method for evaluating a risk of any one of mother's milk and a food inducing an onset of atopic dermatitis, as a substance which binds to the instrument of the present invention, the above-described substance which inactivates coenzyme A may be used in place of the substance which binds to coenzyme A.

The present invention further provides an apparatus used for the method for evaluating a risk of any one of mother's milk and a food inducing an onset of atopic dermatitis of the present invention, or the method for preparing any one of mother's milk and a food with a reduced risk of inducing an onset of atopic dermatitis of the present invention, the apparatus comprising the above-described instrument.

The use of the kit, instrument, or apparatus of the present invention makes it possible to conveniently evaluate a risk of any one of mother's milk and a food inducing an onset of atopic dermatitis, and also to conveniently prepare any one of mother's milk and a food with a reduced risk of inducing an onset of atopic dermatitis.

EXAMPLES

Hereinafter, the present invention will be more specifically described based on Examples. However, the present invention is not to be limited to Examples below.

Note that the materials and methods in the present examples are as follow.

<Cohort>

Targeted were 900 infants born from pregnant women who went to obstetrics in Chiba University Hospital and JFE Kawatetsu Chiba Hospital from January 2007 to May 2008, and who gave the consent to participate in the birth cohort study. Atopic dermatitis (AD) was defined here as eczema with itchiness lasting 2 months or longer based on the questionnaire at 6 months after birth. At 6 months after birth, 55 infants with atopic dermatitis and 55 healthy infants as control were selected, and the Th2 adjuvant activity in mother's milk that had been collected was measured.

<Collecting Mother's Milk>

At several days after birth and 1 month after birth, mother's milk was collected into disposable plastic conical tubes and cryopreserved (−80° C.). The cryopreserved mother's milk was thawed with running water, 1 ml of which was dispensed into each microtube (1.5 ml). By centrifugation at 10,000 g for 10 minutes at 4° C., cells (lower layer) and milk fat (upper layer) were separated from each other. After the milk fat was removed by suction with an aspirator, a clear water-soluble fraction in the middle was collected into a microtube (1.5 ml) and preserved at 4° C.

<Measurement of Intracellular cAMP Concentration>

In a humid incubator under conditions of 37° C. and 5% $CO_2$, THP-1 cells were cultured in an RPMI1640 medium supplemented with 10% fetal bovine serum, 1% penicillin and streptomycin, and 1% L-glutamine. The THP-1 cells were exposed to 50 ng/ml of PMA (phorbol 12-myristate 13-acetate) for 48 hours, followed by washing. Then, the cells were cultured at 37° C. in the presence of 1 mM 3-isobutyl-1-methyl-xanthine. After 10 minutes, the cells were stimulated with 30% mother's milk (AD: n=55, non-AD: n=55) for 10 minutes, and lysed with cell lysis buffer (Molecular Devices). In some experiments, THP-1 cells treated with 50 ng/ml of PMA for 48 hours were exposed to 10 μM prostaglandin $E_2$ ($PGE_2$). The intracellular cAMP level was measured using CatchPoint™ cyclicAMP fluorescent assay kit (Molecular Devices LLC) in accordance with the maker instruction. In some experiments, delta (Δ)-cAMP was calculated by subtracting the cAMP concentration in THP-1 stimulated with PMA without adjuvant stimulation from the cAMP concentration in THP-1 stimulated with PMA with adjuvant stimulation.

<Preparation of Human Monocyte-Derived Dendritic Cells (Mo-DCs) and T lymphocytes>

Human Mo-DCs and CD45RA-positive naive T cells (purity of more than 99%) were prepared according to the previous report (Takagi, R. et al., J Immunol 181: 186-189, 2008).

<Analysis of T Cell-Differentiation Using Dendritic Cells>

The immature Mo-DCs were stimulated with 1 to 10% of a liquid fraction of mother's milk or 0 to 10 μg/ml of coenzyme A. Two days after culturing with the liquid fraction or coenzyme A, to induce a mixed lymphocyte reaction (MLR), the cell component was further cultured together with HLA-DR-nonshared allogenic CD4-positive naive T cells in an RPMI1640 medium supplemented with 10% human serum for 6 to 8 days. Then, the T cells were restimulated with an anti-CD3 antibody and an anti-CD28 antibody (BD Pharmingen Inc.). After 48 hours, the culture supernatant was collected to analyze $IFN_\gamma$ and IL-5 by ELISA using $IFN_\gamma$ and IL-5 ELISA kits (R&D systems, Inc.).

<HPLC Analysis>

The liquid phase of the mother's milk was loaded onto a 4.6×250-mm C8 reversed phase (RP)-HPLC column (Shiseido) equilibrated with 0.06% TFA. While A214 and A280 were continuously monitored, the column was eluted by 0.052% TFA-acetonitrile concentration gradient at a flow rate of 1.0 ml/minute at room temperature. The fractions were concentrated and dried with Speed Vac (Savant Inc.).

<Mass Spectrometry>

The mass spectrum was recorded on a LCMS-IT-TOF mass spectrometer (Shimadzu Corporation) equipped with an electrospray ionization source. The samples were pulse-injected at a flow rate of 0.2 ml/minute using a buffer solution containing a mixture of 50% acetonitrile and 0.1% formic acid. For the operation, the electrospray voltage was set at 4.5 kV, and the capillary temperature was set at 200° C. The neblizing of nitrogen gas was set at 1.5 L/minute. The spectrum was obtained by scanning across the mass/charge (m/z) range from 200 to 1000 every 0.3 seconds for 2 minutes. To integrate the spectra within the scanning time and to calculate the mass within the expected range, a computer program LCMS solution was used.

<Determination of Coenzyme A Concentration>

The concentration of coenzyme A was determined using Coenzyme A Assay kit (BioVision Research Products) in accordance with the maker instruction.

<Mixed Lymphocyte Reaction Using CD3ε-Negative Cells Harvested from Mice to Which Coenzyme A Had been Orally Administered>

SJL/J mice (H-2$^s$) and Nc/Nga mice (non H-2$^s$) were purchased from Charles River Inc. and Japan SLC, Inc., respectively. 50 μg/ml of coenzyme A was orally administered to the SJL/J mice. Two days later, CD3ε-negative cells were obtained from mesenteric lymph node cells using "CD3ε$^{31}$ cell isolation kit" (Miltenyi Biotec Inc.). On the same day, CD62L-positive naive CD4-positive T cells were obtained from the spleens of the Nc/Nga mice using "CD4$^+$ T cell isolation kit" and "CD62L$^+$ T cell isolation kit" (Miltenyi Biotec Inc.). Then, 1×10$^4$ CD3ε-negative cells and 1×10$^5$ allogenic CD62L-positive naive CD4-positive T cells were co-cultured in a 96-well flat-bottomed culture plate. A mixed lymphocyte reaction (MLR) was induced in an RPMI1640 medium supplemented with 10% FCS for 7 days. Next, the T cells were restimulated with an anti-CD3 antibody and an anti-CD28 antibody (Biolegends, Inc.). The culture supernatant were harvested 16 hours later, and analyzed for $IFN_\gamma$, IL-4, and IL-5 using $IFN_\gamma$, IL-4 and IL-5 ELISA kits (R&D systems, Inc.).

Example 1

Purification and Mass Spectrometry of Entity of Th2 Adjuvant Activity in Mother's Milk The present inventors had detected a Th2 adjuvant activity in mother's milk using THP-1 cells as dendritic cells. As a result, it had been found out that in the mother's milk associated with atopic dermatitis, the Th2 adjuvant activity was high based on formation of cAMP (NPL 3). For this reason, the present inventors separated mother's milk by centrifugation into three fractions: a cell-containing pellet, an interface liquid phase, and a surface lipid. These fractions were co-cultured with THP-1 cells treated with PMA, and the cAMP-elevating activity was evaluated. As a result, the cAMP-elevating activity was efficiently recovered in the liquid fraction but not in the pellet and lipid fractions (FIG. 1A). The activity stayed the same, even after the filtration for sterilization.

Next, the present inventors examined the Th1/Th2 cytokine profile in the analysis of T cell-differentiation mediated by dendritic cells. The Mo-DCs were used in this analysis, and stimulated with the filtered liquid phase of the mother's milk. In this analysis, the mother's milk preparation was co-cultured only with the dendritic cells (no T cells were exposed to the mother's milk). LPS and forskolin were used as positive controls of Th1 adjuvant and Th2 adjuvant, respectively (data not shown). As a result, the liquid phase of the mother's milk demonstrated a high $IL-5/IFN_\gamma$ ratio. This revealed that the liquid phase actually acted on the dendritic cells and had an activity of inducing Th2 cell-differentiation (FIG. 1B).

Figure 2:
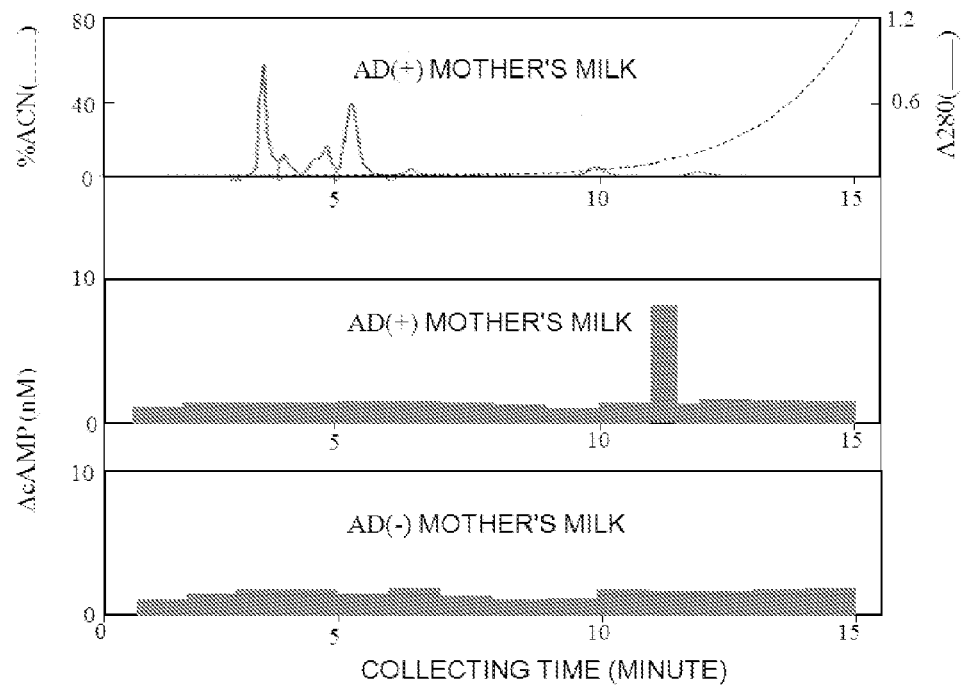
FIG. 2 is graphs showing the result of loading the liquid phase of the mother's milk onto C8 RP-HPLC. The solid line represents A280, and the dotted line represents %ACN.

Thus, next, the present inventors purified the liquid phase of the mother's milk by using C8 reversed phase-HPLC. The cAMP-inducing activities of fractions were determined every 30 seconds. As a result, fractions of 11.0 to 11.5 minutes in mother's milk having a high cAMP inductivity exclusively exhibited the highest activity, whereas fractions of 11.0 to 11.5 minutes in mother's milk having a low cAMP inductivity did not exhibit such a cAMP-inducing activity (FIG. 2). The fractions hardly contained an A280 signal. This suggested that a protein was hardly contained. Fractions of 15 to 25 minutes exhibited A280 signal, but did not exhibit a cAMP-inducing signal (data not shown).

Example 2

Identification of Entity of Th2 Adjuvant Activity in Mother's Milk by Mass Spectrometry The present inventors analyzed the fractions of 11.0 to 11.5 minutes in mother's milk having a high cAMP-inductivity by mass spectrometry. The result revealed that among many detected signals, a signal "Mi=384.7719, Mi+1=385.2754 (Mi+1−Mi=0.5035)" was detected in mother's milk high in the activity, but was not detected in mother's milk low in the activity (Table 1).

TABLE 1

| | Mother's milk | | | | | | | | | |
|---|---|---|---|---|---|---|---|---|---|---|
| | AD(+) infant | | | | | AD(−)infant | | | | |
| Mi | Mi + 1 | Mi + 1 − Mi | v | MW | | Mi | Mi + 1 | Mi + 1 − Mi | v | MW |
| 216.1228 | 217.1273 | 1.0045 | 1 | 215.1155 | | 216.1231 | 217.1149 | 0.9918 | 1 | 215.1158 |
| 599.3896 | 600.3924 | 1.0028 | 1 | 598.3823 | | 599.3895 | 600.3933 | 1.0038 | 1 | 598.3822 |
| 316.2127 | 317.2143 | 1.0016 | 1 | 315.2054 | | 316.2127 | 317.2147 | 1.0020 | 1 | 315.2054 |
| 384.7719 | 385.2754 | 0.5035 | 2 | 767.5292 | | | | | | |
| 430.2440 | 431.2476 | 1.0036 | 1 | 429.2367 | | 430.2454 | 431.2577 | 1.0123 | 1 | 429.2381 |
| 485.3589 | 486.3613 | 1.0024 | 1 | 484.3516 | | 485.3585 | 486.3604 | 1.0019 | 1 | 484.3512 | v: valence number,
MW: molecular weight

The molecular weight of this signal molecule was calculated to be 767.5292 This completely matched the molecular weight of coenzyme A. The same results were obtained in two other experiments on mother's milk preparations. The above suggested that coenzyme A in mother's milk was involved in the Th2 adjuvant activity.

Example 3

Analysis of Th2 Adjuvant Activity of Coenzyme A In Vitro

Figure 3:
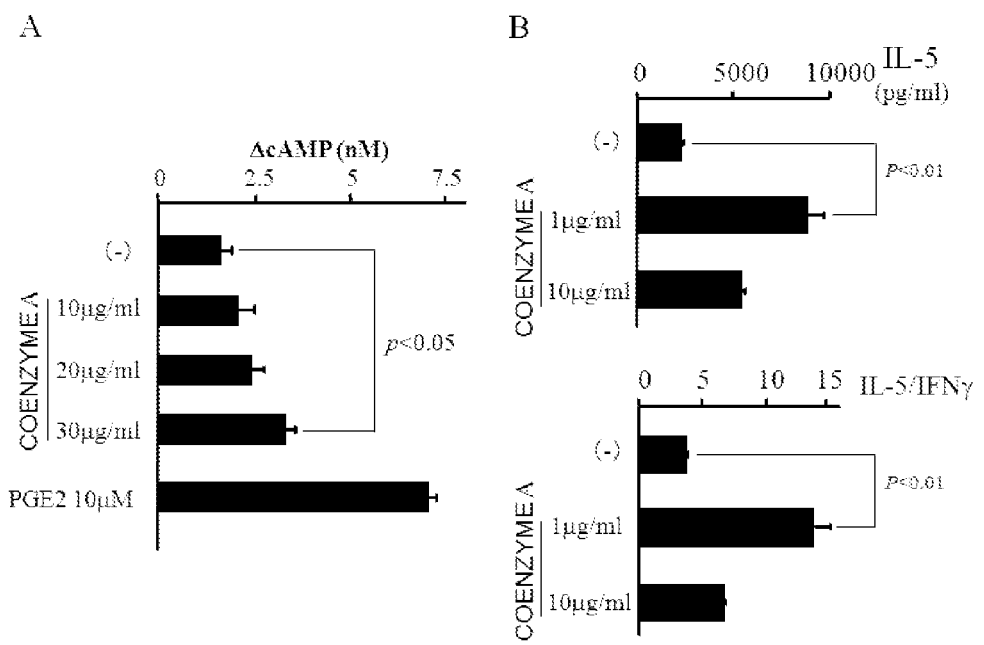
FIG. 3 is graphs showing the result of detecting the Th2 adjuvant activity of coenzyme A in vitro. Part A shows the result of detecting the Th2 adjuvant activity on the basis of cAMP. Part B shows the result of detecting the Th2 adjuvant activity on the basis of IL-5 or IL-5/IFN$_\gamma$.

Next, the present inventors tested the Th2 adjuvant activity of coenzyme A in vitro using dendritic cells. The Th2 adjuvant activity was tested by MLR and change in intracellular cAMP concentration. As a result, the intracellular cAMP of the THP-1 cells treated with PMA was elevated by co-incubating with 10 to 30 µg/ml (13 to 39 µM) of coenzyme A. Further, when Mo-DCs were pretreated with 1 µg/ml of coenzyme A, allogenic naive CD4-positive T cells were differentiated into Th2 cells (FIG. 3B). The above revealed that coenzyme A itself had a Th2 adjuvant activity.

Example 4

Analysis of Th2 Adjuvant Activity of Coenzyme A In Vivo

Figure 4:
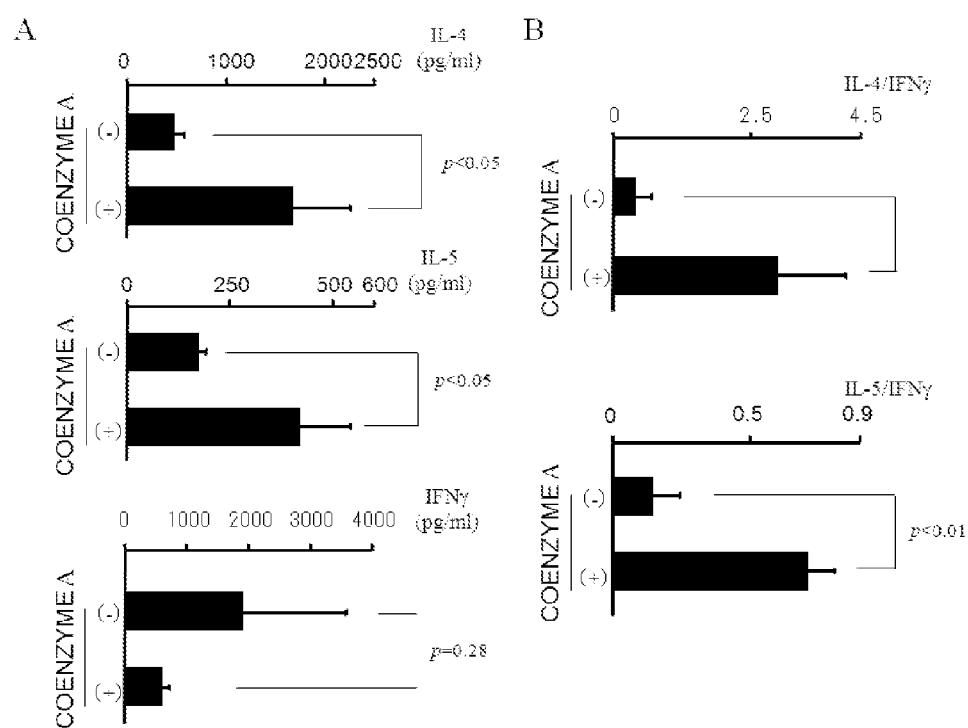
FIG. 4 is graphs showing the result of detecting the Th2 adjuvant activity of coenzyme A in vivo. As for Part A, a mixed lymphocyte reaction was induced by using CD3ϵ-negative cells harvested from mice to which coenzyme A had been orally administered and allogenic naive CD4-positive T cells, and productions of IL-4, IL-5, and IFN$_\gamma$ in the T cells were detected. Part B is graphs representing the Th2 adjuvant activity by IL-4/IFN$_\gamma$ and IL-5/IFN$_\gamma$.

Furthermore, the present inventors tested whether or not coenzyme A exhibited a Th2 adjuvant activity in vivo. Coenzyme A-containing drinking water (10 to 20 µg/kg/day) was orally administered to mice. The dose corresponds to the amount of coenzyme A infants orally took from the mother's milk which exhibited the highest Th2 adjuvant activity. CD3γ-negative cells were isolated from the mesenteric lymph node 2 days after the coenzyme A administration, and co-cultured with allogenic CD62L-positive naive CD4-positive T cells. In this MLR analysis, high concentration IL-4 and IL-5 were significantly induced (FIG. 4A). No statistically significant difference was observed in $IFN_\gamma$ (FIG. 4A). The treated mice had significantly high $IL-4/IFN_\gamma$ ratio and IL-5/IFN ratio (FIG. 4B). The above revealed that coenzyme A had a Th2 adjuvant activity in vivo also.

INDUSTRIAL APPLICABILITY

As described above, the present invention makes it possible to efficiently evaluate a risk of any one of mother's milk and a food inducing an onset of atopic dermatitis by targeting coenzyme A. Moreover, it is made possible to efficiently prepare any one of mother's milk and a food with a reduced risk of inducing an onset of atopic dermatitis by removing or inactivating coenzyme A. Therefore, the present invention can greatly contribute in the medical field, for example, preventing development of atopic dermatitis, and also in the field of foods, for example, developing foods and mother's milk with a reduced risk of inducing an onset of atopic dermatitis.

The invention claimed is:

1. A method for preparing mother's milk with a reduced risk of inducing an onset of atopic dermatitis in an infant, the method comprising:
   providing a mother's milk obtained from a mother whose infant is at risk for atopic dermatitis, wherein the mother's milk comprises coenzyme A at a concentration of 0.5 nM or higher; and
   removing coenzyme A from the mother's milk to a control coenzyme A concentration at least two-fold less than 0.5 nM, wherein the control coenzyme A concentration is determined from a mother's milk whose infant does not develop atopic dermatitis, and wherein the removing step comprises: (i) contacting a liquid phase of the milk with a substance that binds to coenzyme A and (ii) separating coenzyme A from the liquid phase.

2. The method of claim 1, wherein the coenzyme A in said mother's milk having a risk of inducing the onset of atopic dermatitis is present at a concentration of 1 nM or higher.

* * * * *